United States Patent
Armstrong-Ostle et al.

(10) Patent No.: US 11,090,199 B2
(45) Date of Patent: Aug. 17, 2021

(54) METHOD AND APPARATUS FOR MAKING AN ABSORBENT STRUCTURE COMPRISING CHANNELS

(71) Applicant: The Procter & Gamble Company, Cincinnati, OH (US)

(72) Inventors: Peter Armstrong-Ostle, Bonn (DE); Jan Michael Trinkaus, Industriepark am Silberberg (DE); Lothar Volker Kuntze, Swisttal (DE)

(73) Assignee: The Procter & Gamble Company, Cincinnati, OH (US)

( * ) Notice: Subject to any disclaimer, the term of this patent is extended or adjusted under 35 U.S.C. 154(b) by 181 days.

(21) Appl. No.: 16/546,923

(22) Filed: Aug. 21, 2019

(65) Prior Publication Data

US 2019/0374391 A1 Dec. 12, 2019

Related U.S. Application Data

(63) Continuation of application No. 14/615,467, filed on Feb. 6, 2015, now abandoned.

(30) Foreign Application Priority Data

Feb. 11, 2014 (EP) .................................. 14154594
Jan. 19, 2015 (EP) .................................. 15151574

(51) Int. Cl.
*A61F 13/15* (2006.01)
*B32B 37/00* (2006.01)
(Continued)

(52) U.S. Cl.
CPC .. *A61F 13/15634* (2013.01); *A61F 13/15658* (2013.01); *A61F 13/15699* (2013.01);
(Continued)

(58) Field of Classification Search
CPC .......... A61F 13/15634; A61F 13/15658; A61F 13/15699; A61F 13/15764;
(Continued)

(56) References Cited

U.S. PATENT DOCUMENTS

| 1,733,997 A | 10/1929 | Marr |
| 1,734,499 A | 11/1929 | Marinsky |

(Continued)

FOREIGN PATENT DOCUMENTS

| CA | 2001370 | 4/1990 |
| CA | 2291997 | 6/2000 |

(Continued)

OTHER PUBLICATIONS

Extended European Search Report and Search Opinion; Application Ser. No. 15151574.9; dated Mar. 3, 2015; 7 pages.
(Continued)

*Primary Examiner* — Jeffry H Aftergut
(74) *Attorney, Agent, or Firm* — Jay A. Krebs

(57) ABSTRACT

The present invention relates to an apparatus and method for making an absorbent structure for an absorbent article, comprising a supporting sheet and thereon an absorbent layer, the absorbent layer comprising an absorbent material. According to the present invention a first moving endless surface is provided which has one or more substantially longitudinally extending first mating strips, and at least one further auxiliary moving endless surface is provided which acts against the first mating strips. Pressure is applied between the first moving endless surface and the auxiliary moving endless surface to the first and second supporting sheets at least within a part of the area of the channels, so as to adhere together the first and second supporting sheets.

20 Claims, 5 Drawing Sheets

(51) Int. Cl.
*B32B 37/12* (2006.01)
*B32B 37/24* (2006.01)
*B32B 38/18* (2006.01)

(52) U.S. Cl.
CPC .. *A61F 13/15764* (2013.01); *A61F 13/15804* (2013.01); *B32B 37/0046* (2013.01); *B32B 37/1292* (2013.01); *B32B 37/24* (2013.01); *B32B 38/18* (2013.01); *A61F 2013/1591* (2013.01); *B32B 2555/02* (2013.01); *Y10T 156/10* (2015.01); *Y10T 156/1761* (2015.01)

(58) Field of Classification Search
CPC ....... A61F 13/15804; A61F 2013/1591; B32B 37/0046; B32B 37/1292; B32B 37/24; B32B 38/18; B32B 2555/02; Y10T 156/10; Y10T 156/1761
See application file for complete search history.

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Björnbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,059,114 A | 11/1977 | Richards |
| 4,074,508 A | 2/1978 | Reid |
| 4,084,592 A | 4/1978 | Tritsch |
| 4,100,922 A | 7/1978 | Hernandez |
| 4,154,883 A | 5/1979 | Elias |
| 4,211,743 A | 7/1980 | Nauta et al. |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,381,783 A | 5/1983 | Elias |
| 4,388,075 A | 6/1983 | Mesek et al. |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,573,986 A | 3/1986 | Minetola et al. |
| 4,578,072 A | 3/1986 | Lancaster |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,731,066 A | 3/1988 | Korpman |
| 4,731,070 A | 3/1988 | Koci |
| RE32,649 E | 4/1988 | Brandt et al. |
| 4,747,846 A | 5/1988 | Boland et al. |
| 4,773,905 A | 9/1988 | Molee |
| 4,784,892 A | 11/1988 | Storey et al. |

(56) References Cited

U.S. PATENT DOCUMENTS

| | | |
|---|---|---|
| 4,785,996 A | 11/1988 | Ziecker et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,808,178 A | 2/1989 | Aziz |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,076,774 A | 12/1991 | Farrington et al. |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,387,207 A | 2/1995 | Dyer et al. |
| 5,387,209 A | 2/1995 | Yamamoto et al. |
| 5,389,095 A | 2/1995 | Suzuki |
| 5,397,316 A | 3/1995 | Lavon et al. |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,466,409 A | 11/1995 | Partridge et al. |
| 5,476,458 A | 12/1995 | Glaug et al. |
| 5,486,166 A | 1/1996 | Bishop et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,536,341 A | 7/1996 | Kelman |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,560,878 A | 10/1996 | Dragoo et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,607,416 A | 5/1997 | Yamamoto et al. |
| 5,626,571 A | 5/1997 | Young et al. |

(56) References Cited

U.S. PATENT DOCUMENTS

| | | |
|---|---|---|
| 5,628,741 A | 5/1997 | Buell et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,665,396 A | 9/1997 | Ulman |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Ronnberg |
| 6,258,996 B1 | 7/2001 | Goldman |
| 6,265,488 B1 | 7/2001 | Fujino et al. |
| 6,277,226 B1 | 8/2001 | Schulz |
| 6,306,122 B1 | 10/2001 | Narawa et al. |
| 6,315,765 B1 | 11/2001 | Datta |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,419,667 B1 | 7/2002 | Avalon et al. |

(56) References Cited

U.S. PATENT DOCUMENTS

| | | |
|---|---|---|
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Ronnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,734,335 B1 | 5/2004 | Graef |
| 6,790,798 B1 | 9/2004 | Suzuki et al. |
| 6,809,158 B2 | 10/2004 | Ikeuchi et al. |
| 6,818,083 B2 | 11/2004 | Mcamish et al. |
| 6,830,800 B2 | 12/2004 | Curro et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,250,481 B2 | 7/2007 | Jaworek et al. |
| 7,252,657 B2 | 8/2007 | Mishima |
| 7,265,258 B2 | 9/2007 | Hamilton |
| RE39,919 E | 11/2007 | Dodge, II et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |

(56) References Cited

U.S. PATENT DOCUMENTS

| | | | |
|---|---|---|---|
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,021 B2 * | 5/2010 | Venturino ......... A61F 13/15658 |
| | | | 156/73.1 |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,744,576 B2 | 6/2010 | Busam et al. |
| 7,744,578 B2 | 6/2010 | Tanio et al. |
| 7,744,713 B2 | 6/2010 | Blessing et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,133,212 B2 | 3/2012 | Takada |
| 8,148,598 B2 | 4/2012 | Tsang et al. |
| 8,163,124 B2 | 4/2012 | Moriura et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 * | 10/2013 | Jackels ............... A61F 13/4704 |
| | | | 162/297 |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,674,170 B2 | 3/2014 | Busam et al. |
| 8,766,031 B2 | 7/2014 | Becker et al. |
| 8,772,570 B2 | 7/2014 | Kawakami et al. |
| 8,785,715 B2 | 7/2014 | Wright et al. |
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0062112 A1 | 5/2002 | Mizutani |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0114816 A1 | 6/2003 | Underhill |
| 2003/0114818 A1 | 6/2003 | Benecke et al. |
| 2003/0120235 A1 | 6/2003 | Boulanger |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0167045 A1 | 9/2003 | Graef |
| 2003/0171727 A1 | 9/2003 | Graef |

(56) References Cited

U.S. PATENT DOCUMENTS

| | | |
|---|---|---|
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0109442 A1 | 5/2005 | Neubauer et al. |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069371 A1 | 3/2006 | Ohashi et al. |
| 2006/0073969 A1 | 4/2006 | Torii et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0073253 A1 | 3/2007 | Miyama |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0266478 A1* | 10/2009 | Schafer ............. A61F 13/15617 156/229 |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241097 A1 | 9/2010 | Nigam et al. |

(56) References Cited

U.S. PATENT DOCUMENTS

| | | |
|---|---|---|
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1* | 4/2011 | Sagisaka ............ A61F 13/15203 604/385.101 |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | Rinnert et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0324007 A1 | 10/2014 | Hundorf et al. |
| 2014/0324008 A1 | 10/2014 | Hundorf et al. |
| 2015/0223990 A1 | 8/2015 | Armstrong-Ostle et al. |
| 2015/0245954 A1* | 9/2015 | Varga ..................... B32B 37/24 156/64 |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 0203289 A2 | 12/1986 |
| EP | 0206208 | 12/1986 |
| EP | 209561 B1 | 1/1987 |
| EP | 0 226 939 A1 | 7/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0 700 673 A1 | 3/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 863733 | 9/1998 |
| EP | 971751 | 9/1998 |

(56) References Cited

FOREIGN PATENT DOCUMENTS

| | | |
|---|---|---|
| EP | 875224 A1 | 11/1998 |
| EP | 880955 | 12/1998 |
| EP | 891758 | 1/1999 |
| EP | 0893115 | 1/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 1116479 A2 | 7/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1262531 A1 | 12/2002 |
| EP | 1263374 B1 | 12/2002 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 2444046 | 4/2012 |
| EP | 2532328 | 12/2012 |
| EP | 2532329 A1 | 12/2012 |
| EP | 2532332 A1 | 12/2012 |
| EP | 2 586 409 A1 | 1/2013 |
| EP | 2 679 209 A1 | 1/2014 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 03224481 B2 | 10/1991 |
| JP | 04122256 | 4/1992 |
| JP | 06269475 A | 9/1994 |
| JP | 08-98859 | 4/1996 |
| JP | 10328232 | 12/1998 |
| JP | 11033056 A | 2/1999 |
| JP | 11318980 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 03420481 B2 | 11/2001 |
| JP | 2001353174 A | 12/2001 |
| JP | 2002052042 A | 2/2002 |
| JP | 2002065718 | 3/2002 |
| JP | 2002113800 A | 4/2002 |
| JP | 2002065718 A | 5/2002 |
| JP | 2002165832 | 6/2002 |
| JP | 2002165836 | 6/2002 |
| JP | 2002272769 A | 9/2002 |
| JP | 2002325792 A | 11/2002 |
| JP | 2002325799 A | 11/2002 |
| JP | 2002369841 A | 12/2002 |
| JP | 2003153955 A | 5/2003 |
| JP | 2003265524 A | 9/2003 |
| JP | 2003275237 | 9/2003 |
| JP | 2004089269 | 3/2004 |
| JP | 03566012 B2 | 6/2004 |
| JP | 03568146 B2 | 6/2004 |

(56) References Cited

FOREIGN PATENT DOCUMENTS

| | | |
|---|---|---|
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |

(56) References Cited

FOREIGN PATENT DOCUMENTS

| | | |
|---|---|---|
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 05113146 B2 | 10/2012 |
| JP | 05129536 B2 | 11/2012 |
| JP | 05105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO9711659 | 4/1997 |
| WO | WO9717922 | 5/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO200115647 | 3/2001 |
| WO | WO200126596 | 4/2001 |
| WO | WO200207663 | 1/2002 |
| WO | WO200232962 | 4/2002 |
| WO | WO2002064877 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO2003105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | 2012125537 A1 | 9/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013060733 | 5/2013 |
| WO | WO2014078247 | 5/2014 |

OTHER PUBLICATIONS

Third Party Opposition filed for European Patent Application Ser. No. 15151574.9, Aug. 31, 2017; 12 pages.
All Office Actions, U.S. Appl. No. 14/615,467.
CM 4038MQ PCT International Search Report, dated Mar. 27, 2015, 10 pages.

* cited by examiner

METHOD AND APPARATUS FOR MAKING AN ABSORBENT STRUCTURE COMPRISING CHANNELS

CROSS REFERENCE TO RELATED APPLICATION

This application is a continuation of U.S. patent application Ser. No. 14/615,467, filed on Feb. 6, 2015, which claims priority to European Patent Application Nos. EP14154594.7, filed Feb. 11, 2014, and EP15151574.9, filed Jan. 19, 2015.

FIELD OF THE INVENTION

The present invention relates to an apparatus and method for making an absorbent structure with channels embedded within the absorbent structure. The channels are strips that are free of absorbent material.

BACKGROUND OF THE INVENTION

Absorbent articles, such as diapers and sanitary napkins, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine-loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Efforts have also been made to make absorbent article thinner when dry, to improve the comfort of such articles.

Some absorbent articles, like diapers, contain absorbent material such as super absorbent polymers that absorbs very high quantities of liquid and causes the absorbent article to swell significantly. Such articles will thus increase significantly in volume during use, and sometimes in particular in the crotch area between the wearer's legs, which may render the article uncomfortable.

There is thus still a need to further improve the fit of such articles and/or the liquid transportation away from the crotch. There is also a need to reduce the usage of absorbent material in such articles.

There is also still a need to further reduce the chance of leakage and to improve the efficiency of absorbency of an absorbent article, such as a diaper.

It has also been found that improved liquid transportation can be achieved by the provision of transportation channels for distributing liquid in the absorbent article, e.g., the absorbent structure thereof. Furthermore, it has surprisingly been found that the amount of absorbent material can be reduced hereby, whilst maintaining the performance. It has been found that improved fit can be obtained by providing absorbent articles with absorbent structures whereby the absorbent material is structured in machine direction, optionally with areas that comprise less or no absorbent material, for improved bending flexibility in use (in the direction corresponding to the machine direction).

EP-A-2 532 329, published on Dec. 12, 2012, discloses an apparatus and method for producing an absorbent structure comprising at least two supporting sheets and a layer of absorbent material deposited, preferably by a printing process, onto at least one of the supporting sheets. It discloses a separate pressure roll which may selectively apply pressure only onto the channel area of the absorbent structure. The pressure means may comprise raised mating strips.

The present invention relates to an apparatus for making an absorbent structure for an absorbent article, comprising a supporting sheet and thereon an absorbent layer, the absorbent layer comprising an absorbent material, the apparatus comprising:

a) transfer means for transferring first and second supporting sheets to first and second moving endless surfaces;

b) a feeder for feeding the absorbent material onto at least the first supporting sheet at a depositing point on the first moving endless surface, the absorbent material forming absorbent regions upon the supporting sheet, and one or more channels between the absorbent regions, the channels being substantially free of absorbent material;

c) an adhesive applicator for applying adhesive to at least one of the first and second supporting sheets, at least within the region of the channels.

The present invention further relates to a method for making an absorbent structure comprising a supporting sheet and thereon an absorbent layer of absorbent material, the method comprising the steps of:

a) transferring first and second supporting sheets to first and second moving endless surfaces;

b) feeding the absorbent material onto at least the first supporting sheet at a depositing point on the first moving endless surface, the absorbent material forming absorbent regions and one or more channels between the absorbent regions, the channels being substantially free of absorbent material;

c) applying adhesive to at least one of the first and second supporting sheets, at least within the region of the channels.

The present invention addresses the problem of ensuring accurate registration between the pattern of regions free of absorbent material formed in the depositing or printing step, and the pressure applied by separate pressure rolls in a downstream gluing step.

The present invention combines the depositing or printing step and the pressure step which forms the channels by adhesion onto a single moving endless surface, e.g., a roll.

SUMMARY OF THE INVENTION

According to the present invention a first moving endless surface is provided which has one or more substantially longitudinally extending first mating strips, and at least one further auxiliary moving endless surface is provided which acts against the first mating strips. Pressure is applied between the first endless moving surface and the auxiliary moving endless surface to the first and second supporting sheets at least within a part of an area of the channels, so as to adhere together the first and second supporting sheets.

According to a preferred embodiment of the present invention, second and third auxiliary moving endless surfaces are provided such that the first moving endless surface which carries the first and second supporting sheets passes under pressure between the second and third auxiliary moving endless surfaces.

DETAILED DESCRIPTION OF THE INVENTION

Figure 1A:
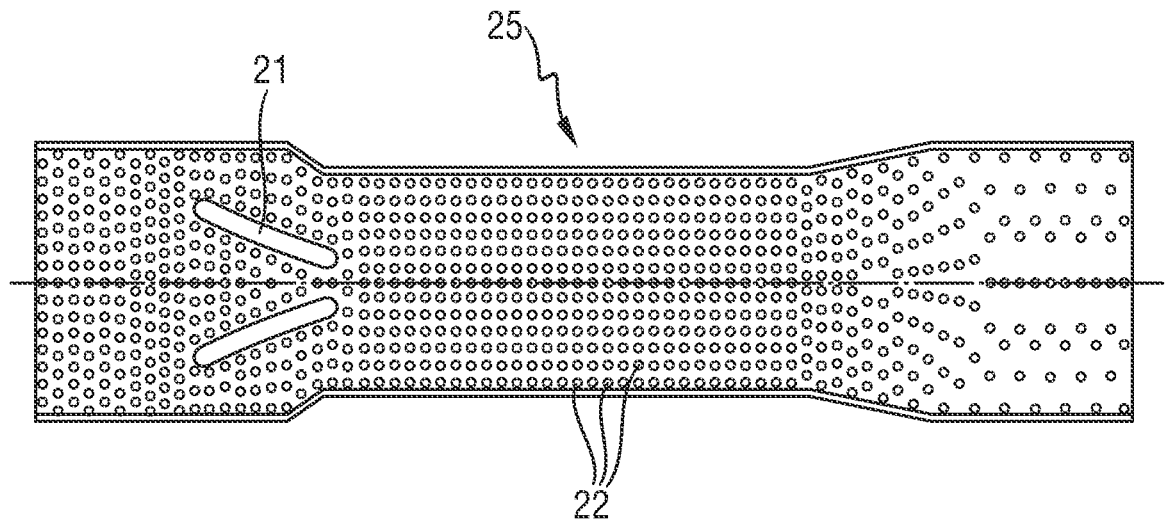
FIG. 1A is a top view of a reservoir 25.

As summarized above, this invention encompasses a method and apparatus for making an absorbent structure useful for an absorbent article comprising absorbent material, preferably comprising at least, or only, particulate superabsorbent polymer material. Embodiments of such method and apparatus and resulting absorbent structures and absorbent articles are further described herein, after the following definitions.

Definitions

"Absorbent structure" refers to a three-dimension structure with a longitudinal dimension and, perpendicular thereto, a transverse dimension, and, perpendicular to both, a height dimension, and that comprises at least an absorbent material and a supporting sheet, and that is useful in an absorbent article.

"Absorbent layer" refers to a three dimensional layer of absorbent material, formed by deposition of absorbent material onto the supporting sheet.

"Absorbent material" refers to a material or mixture of materials that can absorb and retain bodily fluids; it typically includes or consists of "superabsorbent polymer material".

"Superabsorbent polymer material" (also known as "absorbent gelling material," or "AGM," or "superabsorbent,") refer to polymeric material that can absorb at least 10 times (and typically at least 15 times, or at least 20 times) their weight of an aqueous 0.9% saline solution as measured using the Centrifuge Retention Capacity test (Edana 441.2-02), i.e. having a CRC of at least 10 g/g, and typically at least 15 g/g or at least 20 g/g.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diapers, including pants, such as infant training pants and adult incontinence undergarments, and feminine hygiene products, such as sanitary napkins and panty-liners and adult incontinent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

"Diaper" refers to an absorbent article generally worn by infants and incontinent persons about the lower torso so as to encircle the waist and legs of the wearer and that is specifically adapted to receive and contain urinary and fecal waste.

"Pant" or "training pant", as used herein, refer to diaper having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Particulate" is used herein to refer to a material which is in particulate form so as to be flowable in the dry state.

"Substantially cellulose free" is used herein to describe an article, such as an absorbent layer structure or core, that contains less than 5% by weight cellulosic fibers.

"Thickness" and "height" are used herein interchangeably.

According to the present invention absorbent material 100 may be fed onto the supporting sheet 16, 16' by any suitable means including gravimetric feeding or by using a print roll. In the embodiment illustrated in FIGS. 1A, 1B and 2 the print roll method is used which is described in more detail below.

Figure 1B:
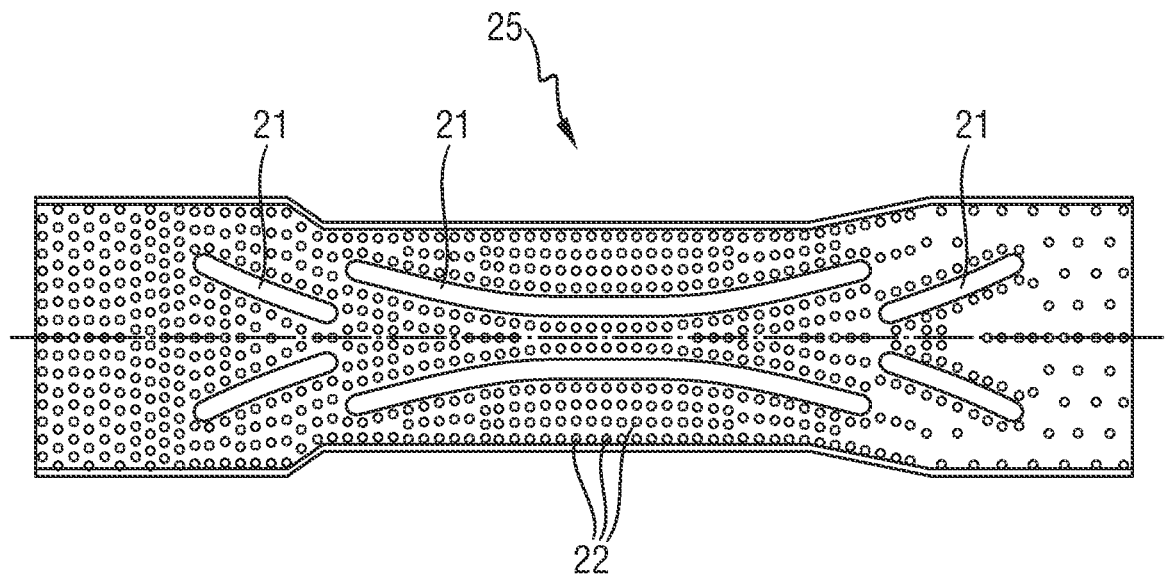
FIG. 1B is a top view of an alternative reservoir 25.

FIGS. 1A and 1B illustrate examples of patterns which provide a reservoir 25 for holding absorbent material prior to depositing, or printing the absorbent material onto a supporting web. Absorbent material is fed to the reservoir, the reservoir holds absorbent material in each of the holes or cavities 22. The reservoirs contain one or more channels 21 between the absorbent regions, the channels 21 being substantially free of absorbent material.

Figure 2:
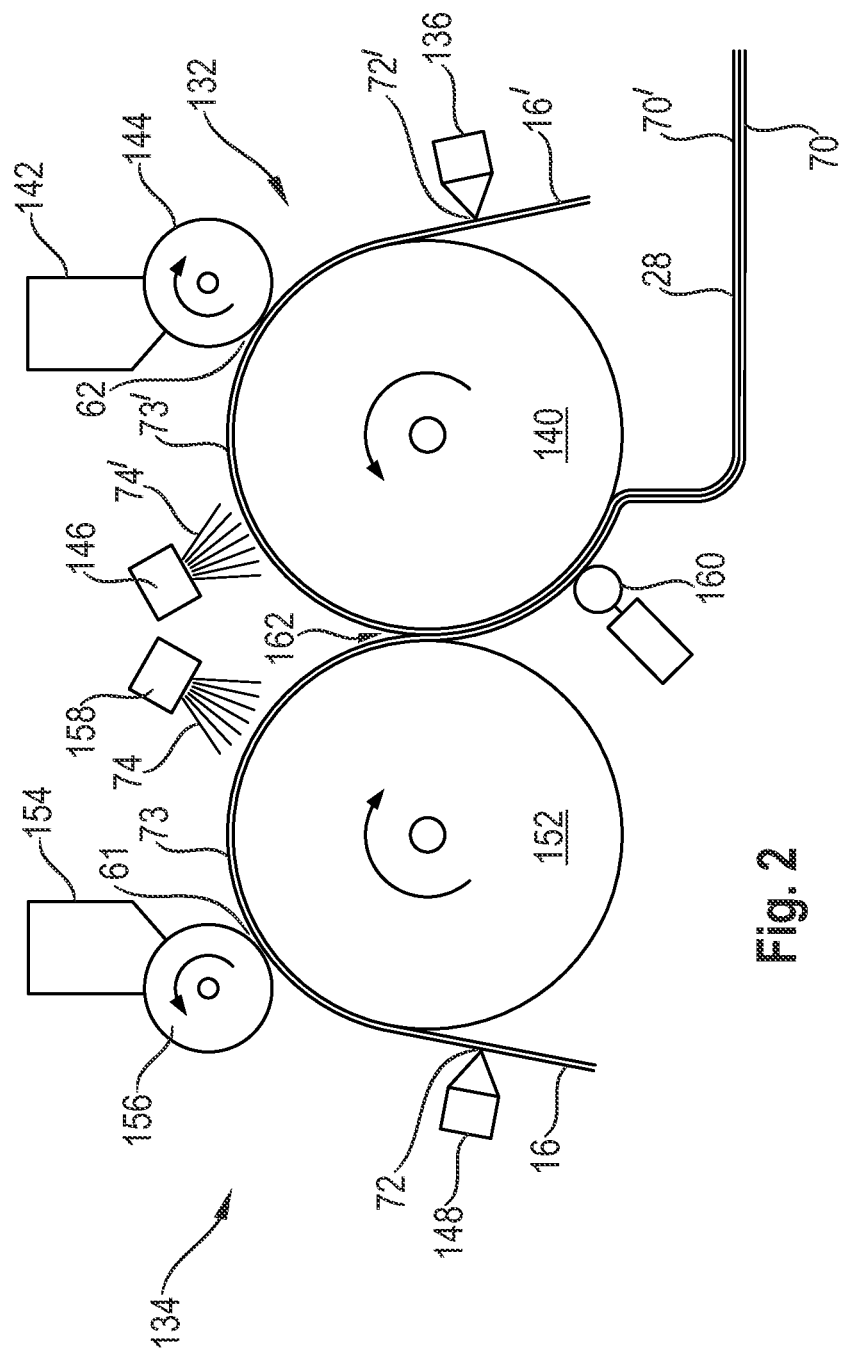
FIG. 2 is a side view of an apparatus of the present invention, or used in the method of the invention.
Figure 3:
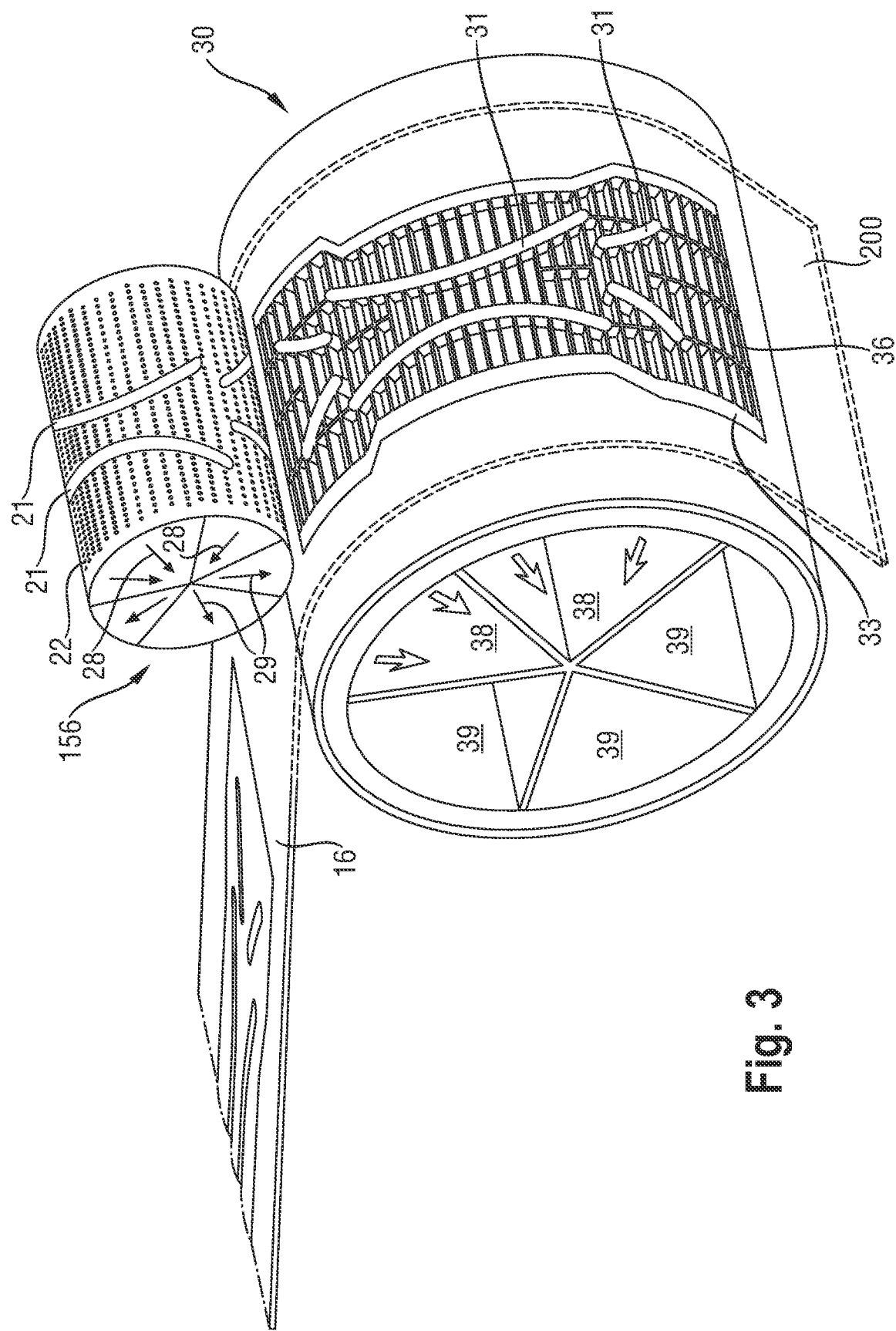
FIG. 3 is a partial perspective view of an apparatus of the present invention, or used in a method of the invention.

In a preferred embodiment of the invention illustrated in FIGS. 2 and 3 the reservoirs are disposed around the outer surface of print rolls 144, 156. The absorbent material 100 is delivered to the supporting sheet 16 by a roll 156 placed adjacent and in close proximity to the first moving endless surface 30, for example substantially above the surface. The absorbent material 100 may be deposited substantially continuously. The point or area where the absorbent material 100 leaves the roll 156 and transfers to the first moving endless surface 30 is herein referred to as the depositing point or area; and in this point or area a raised strip 21, e.g., each raised strip, mates with a mating strip 31, e.g. without direct contact.

A first printing unit 134 for making an absorbent structure in accordance with the first aspect of this invention is illustrated on the left half in FIG. 2. A second printing unit 132 for forming a second absorbent structure is represented on the right side of FIG. 2, both absorbent structures being then combined into an absorbent core in the nip 162.

The first printing unit 134 comprises an auxiliary adhesive applicator 148 for applying an auxiliary adhesive to the substrate 16, a first rotatable support roll 152 for receiving the first substrate 16, a first hopper 154 for holding the absorbent particulate polymer material, a first printing roll 156 for transferring the absorbent particulate polymer material from the hopper 154 to the substrate 16, and a thermoplastic adhesive material applicator 158 for applying the fibrous thermoplastic adhesive material 74 to the first substrate 16 and the absorbent particulate polymer material land areas thereon.

The auxiliary adhesive applicator 148 may be a nozzle system which can provide a relatively thin but wide curtain of thermoplastic adhesive material as suggested in WO 2008/155699, but may instead advantageously comprise a slot coater for applying several slots of auxiliary adhesive simultaneously along the width of the substrate and fitted with a manifold to intermittently stop the delivery of the auxiliary adhesive so that there the auxiliary layer is not applied in the area of the substrate corresponding to the zones of lower absorbent material amount. The printing roll 156 and adhesive applicator 158 may be as further detailed in WO 2008/155699. The absorbent structure 70 obtained by the printing unit 134 may be directly put in face to face relation with a second substrate 16', or may be combined with a second absorbent structure 70' to form an absorbent core. This second absorbent structure 70' may be formed on the second printing unit 132 as shown in FIG. 2, which may be generally identical to the first printing unit 134. The second printing unit 132 may comprise a second auxiliary adhesive applicator 136 which may be a slot coater for applying an auxiliary adhesive to the substrate 16', a second rotatable support roll 140 for receiving the substrate 16', a second hopper 142 for holding absorbent particulate polymer material, a second printing roll 144 for transferring the absorbent particulate polymer material to the substrate 16', and a thermoplastic adhesive material applicator 146 for applying the thermoplastic adhesive material 74' to the substrate 16' and the absorbent particulate polymer land areas thereon.

The radius of the roll 156 may depend on what absorbent structure is produced, e.g. what size, and for example how many structures are produced per cycle of the print roll or drum. For example, the drum/print roll may have a radius of at least 40 mm, or of at least 50 mm; it may be for example up to 300 mm, or up to 200 mm. In some embodiments, the radius of the drum/print roll is less than 50% of the radius of the first moving endless surface. In a preferred embodiment the radius of the print roll is from 60 mm to 80 mm.

The roll 156 may have any suitable width, but for example a width (for example in CD, hence perpendicular to MD) corresponding (substantially) to the width of the absorbent structure to be produced; this for example be at least 40 mm, or at least 60 mm, or for example up to 400 mm, or up to 200 mm.

The roll 156 may have one or more reservoirs 25 with a certain volume for receiving the absorbent material 100 therein, and transporting it to and then depositing it on the supporting sheet 16 on the first moving endless surface.

Each reservoir 25 corresponds typically to an absorbent structure to be produced, as suitable for an absorbent article.

Figure 4:
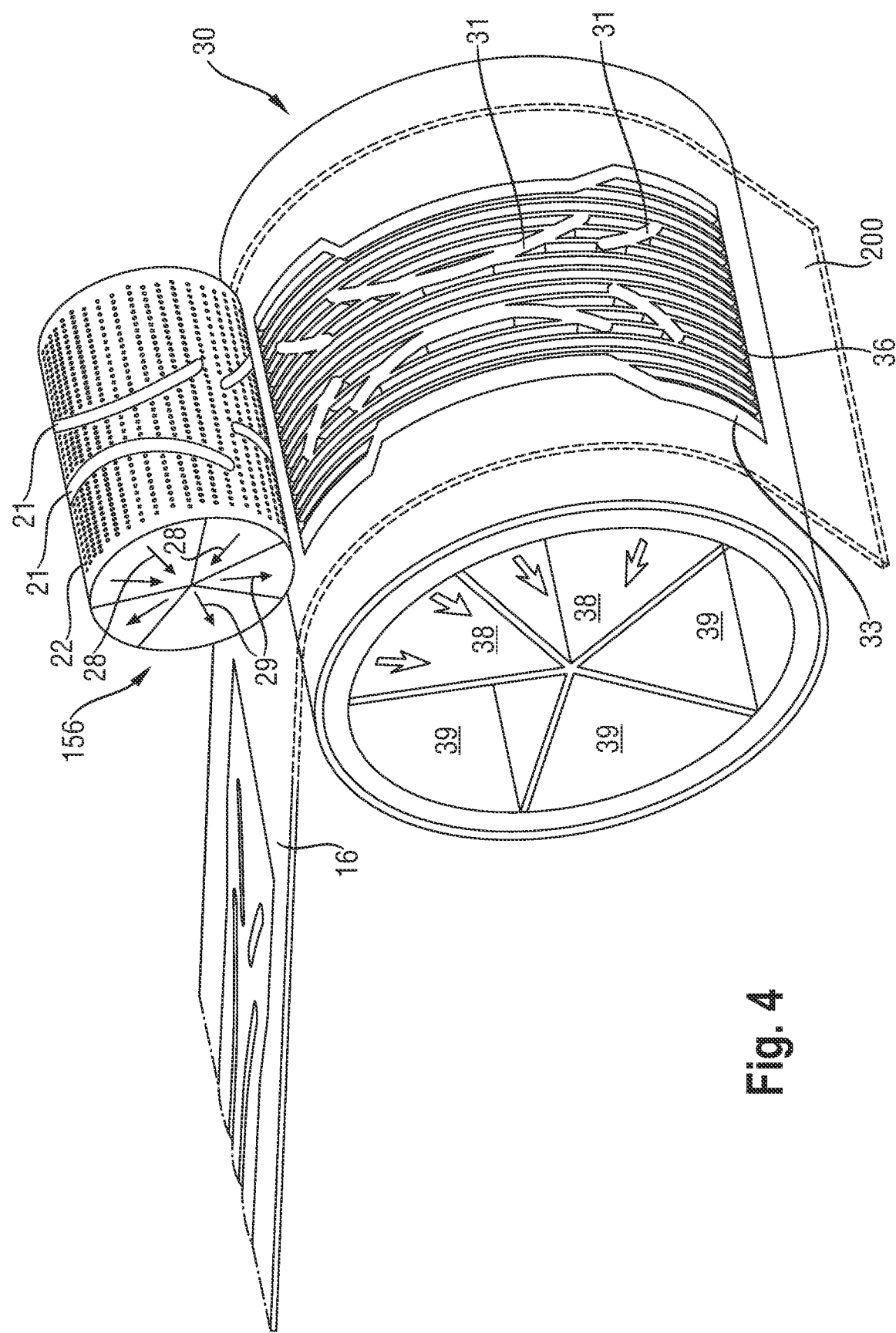
FIG. 4 is a partial perspective view of an alternative apparatus of the present invention, or used in an alternative method of the invention.

According to the present first and second supporting sheets are carried on first and second moving endless surfaces. In FIGS. 2 to 4 these first and second moving endless surfaces are illustrated by drums, referred to herein as lay-down drums 140, 152. Alternatively the moving endless surfaces could be belts.

The supporting sheets 16, 16' are preferably sheets of nonwoven material. Absorbent material is deposited onto at least one, and preferably both, of the supporting sheets from the roll 156, except in the regions corresponding to the raised strips 21 and the mating strips 31.

The first roll 152 has one or more substantially longitudinally extending first mating strips 31, and the second roll 140 has corresponding longitudinally extending second mating strips. Pressure is applied through the first mating strips against an auxiliary bonding roll 160 to the first and second supporting sheets 16, 16' at least within a part of the area of the channels, so as to adhere together the first and second supporting sheets.

By applying pressure to the supporting sheets in this manner, between the first mating strips and the auxiliary bonding roll, rather than by separate pressure rolls positioned downstream of the rolls, the problem of registration of the channel is avoided. Quality control of the absorbent structure is more easily provided, especially in high speed manufacturing processes.

In some embodiments, the first and second moving endless surfaces 140, 152 may for example have a speed of at least 1000, or at least 1200 parts per minute and/or a linear speed of at least 4.5 m/s, or at least 6 m/s, or at least 8 m/s, or at least 10 m/s.

Lay-Down Drum

FIG. 3 illustrates the side-by side arrangement of the print roll 156 and the lay-down drum 152. In the embodiment illustrated in FIG. 3 the drum is a rotating cylindrical drum. The outer shell rotates around a stationary inner chamber, e.g. a stator. The rotating outer shell carries one or more receptacles 33 which receive absorbent material from the print roll 156.

Preferably the receptacle 33 is at least partially air-permeable. It may have an area that serves to receive the absorbent material, and this area is substantially in air-communication with a vacuum system via vacuum chambers 38. This arrangement holds the supporting sheet 16 onto the surface of the lay-down drum 30, and may also hold the absorbent material received from the print roll 156 in place against the surface of the supporting sheet 16, if the supporting web is air permeable.

In one embodiment, not illustrated, the receptacle area 33 other than the mating strips 31 is a mesh material that has apertures, is air permeable, and is in air communication with the chambers 38 of the vacuum system.

In the embodiment of FIG. 3 the surface area of the receptacle 33, other than the mating strips 31, comprises thin supports substantially in transverse direction, for supporting the supporting sheet 16. Typically the maximum dimension in the longitudinal direction is less than the average width dimension of the adjacent mating strip; for example at most 4 mm, preferably at most 3 mm.

In the embodiment of FIG. 4, the receptacle 33 comprises a multitude of substantially longitudinally extending rods 36, spaced apart from one another, and typically from a neighbouring mating strip, in transverse direction. Such rods 36 may then partially form the most outer surface of the receptacle 33, so that the supporting sheet 16 is received and carried by the rods 36 and the mating strips 31.

Pressure is applied between the corresponding first mating strips on the lay-down drum and the auxiliary bonding roll 160 which presses against the first and second supporting webs, specifically in the regions in which the absorbent structure is free of any absorbent material. The combination of pressure and adhesive material between the supporting webs causes the supporting webs to adhere together in these regions and thus forms one or more channels. The application of pressure can be accurately registered with the regions which are free of absorbent material because both the deposit of absorbent material and the application of pressure take place on the same surface, namely the lay-down drum, receptacle 33. It is preferred to avoid applying any pressure to the absorbent material which is sandwiched between the supporting webs. Such pressure could cause absorbent material particles to damage or even puncture or tear the supporting web. Such pressure acting on absorbent material particles between the mating surfaces could also cause undue wear to the mating surfaces. For this reason the area over which pressure is applies between the mating surfaces is preferably slightly narrower and preferably also slightly shorter than the region in which the absorbent material is free of any absorbent material.

Preferably the first mating strips 31 are made from a metallic material, preferably steel and the auxiliary bonding roll is made from an elastic material, preferably silicone, or vice versa.

Process Control

In a preferred embodiment the process is controlled in order to maintain the desired pressure between the mating strips on the lay-down drum and the corresponding mating strips on the auxiliary bonding roll 160. The applied pressure is an important process parameter for achieving required channel bond strength in the finished article. In the description that follows reference is made to pressure applied between two drums, however the principles may equally be applied to other forms of moving endless surfaces, such as belts, rollers, and combinations thereof.

Preferably pressure is applied by means of the mating strips which form part of the outer surface of the drum 30 and the auxiliary bonding roll 160. Each drum is mounted on a shaft, and each shaft is rotated at a set speed by means of a drive, for example an electric motor. Alternatively the auxiliary bonding roll 160 may be rotated by the contact between the drum 30. Each shaft is supported in a backplate which, in turn, is mounted directly or indirectly in the machine frame.

According to the preferred bonding system, the drum 30 has a fixed axis, whilst the axis of auxiliary bonding roll moveable, with the axis of the drum and auxiliary bonding roll staying parallel. Preferably the auxiliary bonding roll is pressed against the surface of the drum with a controlled force greater than 20N, preferably between 50-3000N. Preferably the applied pressure is controlled pneumatically, by adjusting the distance between the drum and the auxiliary bonding roll, for example by means of cylinder air pressure.

Figure 5B:
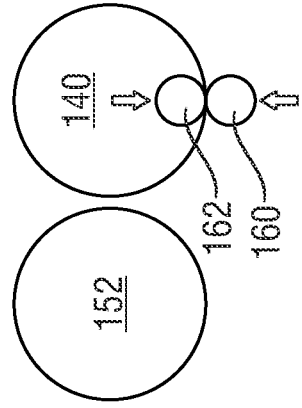
FIG. 5B is a schematic representation of an alternative embodiment comprising two opposing auxiliary bonding rolls.
Figure 5D:
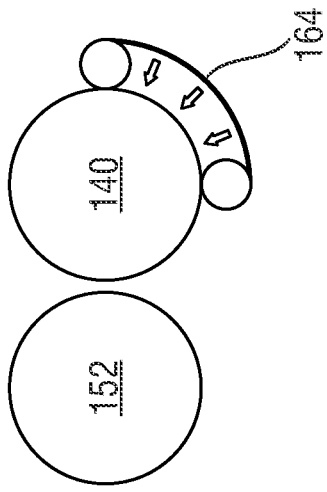
FIG. 5D is a schematic representation of another alternative embodiment comprising an auxiliary bonding belt.
Figure 5A:
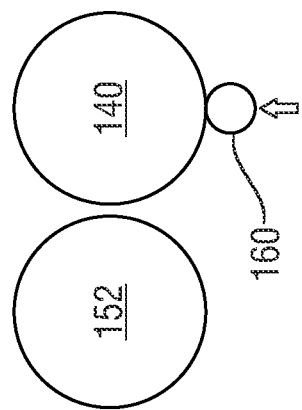
FIG. 5A is a schematic representation of a single auxiliary bonding roll.
Figure 5C:
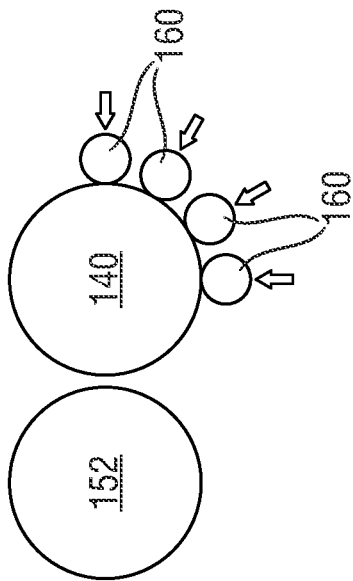
FIG. 5C is a schematic representation of another alternative embodiment comprising an auxiliary bonding roll and opposing support roll.

In alternative embodiments the pressure may be applied between two auxiliary bonding rolls 160, 161, as in FIG. 5B, or by means of two or more auxiliary bonding rolls 160, as in FIG. 5C, or by means of a belt 164, as in FIG. 5D.

The preferred process pressure between the lay-down drum and the auxiliary bonding roll is from 0.3 to 0.8 MPa.

The drums are mounted onto the shaft and the free end of the shaft is referred to as the outside section of the shaft, whereas the opposing end of the shaft is referred to as the drive-side section of the shaft.

Absorbent Material

The absorbent material 100 herein is preferably a flowable material, in the dry state, most preferably a particulate material. In particulate form the absorbent material may be particles, flakes, fibers, spheres, agglomerated particles and other forms known in the art.

The absorbent material 100 comprises superabsorbent polymer material, optionally combined with cellulosic material, including for example cellulose, comminuted wood pulp in the form of fibers. In some embodiments, the absorbent material 100 may comprise at least 60%, or at least 70% by weight of superabsorbent polymer material, and at the most 40% or at the most 30% of cellulosic material. In preferred embodiments, the absorbent layer comprises absorbent material 100 that consists substantially of absorbent polymer material, e.g., less than 5% by weight of the absorbent material of cellulosic material is present; and the absorbent layer/absorbent structure, may be substantially or even completely free of cellulosic material.

In preferred embodiments herein, the absorbent material is a superabsorbent polymer material, herein referred to as SAP, and also known as particulate absorbent gelling material, AGM. The particulate SAP herein may have a high sorption capacity, e.g. having a CRC of for example at least 20 g/g, or at 30 g/g. Upper limits may for example be up to 150 g/g, or up to 100 g/g.

The particulate SAP may have a good permeability for liquid, for example, having a SFC value of at least $10 \times 10^{-7}$ $cm^3$ s/g; or preferably at least $30 \times 10^{-7}$ $cm^3$ s/g, or at least $50 \times 10^{-7}$ $cm^3$ s/g $10 \times 10^{-7}$ $cm^3$ s/g, or possibly permeability SFC value of at least $100 \times 10^{-7}$ $cm^3$ s/g, or at least a SFC of $120 \times 10^{-7}$ $cm^3$ sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or up to 250 ($\times 10^{-7}$ $cm^3$ s/g).

In some embodiments herein the polymers of the SAP are internally cross-linked and/or surface crosslinked polymers.

In some embodiments herein, the absorbent material 100 comprising or consisting of particles of polyacrylic acids/polyacrylate polymers, for example having a neutralization degree of from 60% to 90%, or about 75%, having for example sodium counter ions, as known in the art; they may be surface crosslinked and/or internally crosslinked polyacrylic acid/polyacrylate polymers.

In some embodiments herein, the absorbent material 100 is in the form of particles with, a mass medium particle size up to 2 mm, or between 50 microns and 2 mm or to 1 mm, or preferably from 100 or 200 or 300 or 400 or 500 μm, or to 1000 or to 800 or to 700 μm; as can for example be measured by the method set out in for example EP-A-0691133. In some embodiments of the invention, the material is in the form of particles of which at least 80% by weight are particles of a size between 50 μm and 1200 μm and having a mass median particle size between any of the range combinations above. The particles may be essentially spherical, or may have some other shape. Preferably the absorbent material 100 has a relatively narrow range of particle sizes, e.g., with the majority (e.g., at least 80% or preferably at least 90% or even at least 95% by weight) of particles having a particle size between 50 µm and 1000 µm, preferably between 100 µm and 800 µm, and more preferably between 200 µm and 600 µm.

The absorbent material 100 herein may advantageously comprise less than 15% by weight of water, or less than 10%, or less than 8% or less than 5%. The water-content can be determined by the Edana test, number ERT 430.1-99 (February 1999) which involves drying the particulate material 100 at 105° Celsius for 3 hours and determining the moisture content by the weight loss of the particulate material 100 after drying.

The particulate SAP herein may be particles of SAP that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Supporting Sheet

The absorbent structure produced with the apparatus 1 and method of the invention comprises a supporting sheet 200, to receive the absorbent material. This supporting sheet 200 may be any individual sheet or web sheet material, in particular paper, films, wovens or nonwovens, or laminate of any of these.

In some embodiments herein, the supporting sheet 200 is a nonwoven, e.g., a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g., with different polymers forming the sheet and the core. Nonwoven fabrics can be formed by many processes such as meltblowing, spunbonding, solvent spinning, electrospinning, and carding.

The nonwoven herein may be made of hydrophilic fibers; "Hydrophilic" describes fibers or surfaces of fibers, which are wettable by aqueous fluids (e.g., aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e., hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet 200 herein may be air-permeable. Films useful herein may therefore comprise micro pores. Nonwovens herein may for example be air permeable. The supporting sheet 200 may have for example an air-permeability of from 40 or from 50, to 300 or to 200 $m^3/(m^2 \times min)$, as determined by EDANA method 140-1-99 (125 Pa, 38.3 $cm^2$). The supporting sheet 200 may alternatively have a lower air-permeability, e.g. being non-air-permeable, to for example be better detained on a moving surface comprising vacuum.

In preferred executions, the supporting sheet 200 is a nonwoven laminate material, a nonwoven laminate web, for example of the SMS or SMMS type.

The basis weight of nonwoven fabrics is usually expressed in grams per square meter (gsm). The supporting sheet 200 may have a basis weight that is less than 60 gsm, or for example than 50 gsm, for example from 5 gsm to 40 gsm, or to 30 gsm.

The supporting sheet 200 may have a transverse-extensibility or a longitudinal-extensibility, for example of more the 20%, or for example more than 100%, but for example not more than 200%.

In one of the embodiment herein, the supporting sheet 200 has a transverse dimension that is more than the transverse dimension of the part of the receptacle (33), e.g. at least 10%, or for example at 20% or at least 30%, and for example up to about 120%.

Adhesive Application Units and Method Steps

The supporting sheet 200 is treated with an adhesive prior to, at, and/or after transfer to the moving endless surface. Thus, the apparatus 1 herein comprises adhesive application unit(s) 50, 51. The method herein also comprises such an adhesive application step.

This adhesive may be applied uniformly and/or continuously, to aid absorbent material 100 immobilization and then it may help to adhere the supporting sheet 200 to a further material that may overlay the absorbent layer, as described below. Alternatively, it may be applied in a pattern. It may be applied by spraying, or for example by selectively slot-coating; the apparatus 1 may thus comprise a slot-coater, with a pattern.

The adhesive may be applied on those portions of the supporting sheet 200 that are to receive to receive the absorbent material; then, it helps to immobilize the absorbent material 100 thereon (e.g., to ensure the absorbent material 100 will stay substantially as applied, with the channels, preferably not only during manufacturing, but also during storage and in use (at least during part of the use). Or, alternatively, only on those portions of the supporting sheet 200 that are to be on the mating strips 31; then it may help to adhere the supporting sheet 200 to a further material that may overlay the absorbent layer, as described below. It may be applied as substantially longitudinal stripes, for example.

In some embodiments, the apparatus 1 may comprise a unit to apply an adhesive to the supporting sheet 200 in a pattern, for example the pattern of the mating strips 31, and optionally of the rods 36, if present.

Any suitable adhesive can be used for this, for example so-called hotmelt adhesives used, for example, sprayable hot melt adhesives, such as H.B. Fuller Co. (St. Paul, Minn.) Product No. HL-1620-B, can be used.

Alternatively, or in addition, it may be beneficial to apply a further immobilization adhesive to the absorbent structure produced by the apparatus 1 or method herein, e.g. to ensure the absorbent material 100 will stay substantially as applied, with the channels, preferably not only during manufacturing, but also during storage and in use (at least during part of the use). This immobilization adhesive may then for example be applied onto the absorbent layer just after application of the absorbent material 100 onto the supporting sheet 200.

The apparatus 1 herein may optionally have a further adhesive application unit 50, e.g., downstream from the absorbent material deposition point. The method may have a corresponding method step This adhesive may be applied uniformly and/or homogeneously. This may be a thermoplastic adhesive material.

In accordance with certain embodiments, the thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$<$Tg$<16°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%. In certain embodiments, the thermoplastic adhesive material is present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Test Method

According to the apparatus and method of the present invention, an adhesive bond is formed between first and second supporting sheets in at least a part of the channel area. The bond strength of the adhesively connected regions may be measured by various test methods. A preferred test method is the peel strength test method as described in ASTM D-903-98. In case the standard peel rate of 152 mm (6 inches)/minute results in the tearing of the fragile supporting sheet, then this rate may need to be reduced. 10 mm/minute is preferred.

One suitable power-driven machine for use in the test is a vertical single column Zwick Tensile Tester Test machine with 50 N force cell with force accuracy of 0.3% and distance accuracy of 0.15%. The four faces of the two jaws should be padded with a thin strip of rubber to prevent slippage as provided by the supplier of the equipment (jaws: Vulkollan glatt 30×60 mm, material number 314366, provider: Zwick GmbH & Co, D-89079 Ulm).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an absorbent core, the method comprising steps of:
   rotating a first drum and a second drum in opposite directions, the first drum positioned proximate the second drum to define a nip therebetween, the first drum and the second drum each comprising a mating strip;
   advancing a first supporting sheet on the rotating first drum;
   depositing absorbent material on the first supporting sheet while advancing on the first drum except in a region corresponding to the mating strip to form a first absorbent structure comprising a channel between absorbent regions, the channel being substantially free of absorbent material;
   advancing a second supporting sheet on the rotating second drum;
   depositing absorbent material on the second supporting sheet while advancing on the second drum except in a region corresponding to the mating strip to form a second absorbent structure comprising a channel between absorbent regions, the channel being substantially free of absorbent material;
   applying adhesive to at least one of the first supporting and the second supporting sheet;
   combining the first absorbent structure and the second absorbent structure at the nip; and
   bonding the channel of the first absorbent structure together with the channel of the second absorbent structure with the adhesive by advancing the combined first and second absorbent structures between a bonding roll and the mating strip of the first drum, wherein pressure is applied to an area of the first and second absorbent structures that is narrower and shorter than the channels.

2. The method of claim 1, wherein the absorbent material is a particulate superabsorbent polymer material.

3. The method of claim 1, wherein the step of applying adhesive is performed prior to the steps of depositing absorbent material on the first supporting sheet and depositing absorbent material on the second supporting sheet.

4. The method of claim 1, wherein the step of applying adhesive is performed subsequent to the steps of depositing absorbent material on the first supporting sheet and depositing absorbent material on the second supporting sheet.

5. The method of claim 1, wherein the mating strips of the first and second drums are made from steel.

6. The method of claim 1, wherein the mating strips of the first and second drums are made from silicone.

7. The method of claim 1, wherein the drum comprises an outer shell that comprises an air permeable receptacle for receiving the first supporting sheet thereon, and wherein the outer shell is connected to a vacuum system for facilitating retention of the first supporting sheet and the absorbent material thereon.

8. The method of claim 7, wherein the receptacle further comprises a multitude of substantially longitudinally extending rods, spaced apart from one another in a transverse direction, each rod having a maximum width dimension of at least about 0.3 mm and less than about 2.5 mm, the rods each having an average height dimension of at least about 1 mm.

9. The method of claim 1, wherein the step of depositing absorbent material on the first supporting sheet further comprises transferring the absorbent material from a feeder comprising a reservoir formed by a plurality of cavities.

10. A method for making an absorbent core, the method comprising steps of:
rotating a first drum and a second drum in opposite directions, the first drum positioned proximate the second drum to define a nip therebetween, the first drum and the second drum each comprising a mating strip;
advancing a first supporting sheet on the rotating first drum;
depositing absorbent material on the first supporting sheet while advancing on the first drum except in a region corresponding to the mating strip to form an absorbent structure comprising a channel between absorbent regions, the channel being substantially free of absorbent material;
advancing a second supporting sheet on the rotating second drum;
applying adhesive to at least one of the first supporting and the second supporting sheet;
combining the absorbent structure and the supporting sheet at the nip; and
bonding the channel of the absorbent structure together with the second supporting sheet with the adhesive by advancing the combined absorbent structure and second supporting sheet between a bonding roll and the mating strip of the first drum or the second drum, wherein pressure is applied to an area of the first supporting sheet and the second supporting sheet that is narrower and shorter than the channels.

11. The method of claim 10, wherein the absorbent material is a particulate superabsorbent polymer material.

12. The method of claim 10, wherein the step of applying adhesive is performed prior to the step of depositing absorbent material on the first supporting sheet.

13. The method of claim 10, wherein the step of applying adhesive is performed subsequent to the step of depositing absorbent material on the first supporting sheet.

14. The method of claim 10, wherein the mating strips of the first and second drums are made from steel.

15. The method of claim 10, wherein the mating strips of the first and second drums are made from silicone.

16. A method for making an absorbent core, the method comprising steps of:
rotating a first drum and a second drum in opposite directions, the first drum positioned proximate the second drum to define a nip therebetween, the first drum and the second drum each comprising a mating strip;
advancing a first supporting sheet on the rotating first drum;
depositing absorbent material on the first supporting sheet while advancing on the first drum except in a region corresponding to the mating strip to form a first absorbent structure comprising a channel between absorbent regions, the channel being substantially free of absorbent material;
advancing a second supporting sheet on the rotating second drum;
depositing absorbent material on the second supporting sheet while advancing on the second drum except in a region corresponding to the mating strip to form a second absorbent structure comprising a channel between absorbent regions, the channel being substantially free of absorbent material;
applying adhesive to at least one of the first supporting and the second supporting sheet;
combining the first absorbent structure and the second absorbent structure at the nip; and
bonding the channel of the first absorbent structure together with the channel of the second absorbent structure with the adhesive by advancing the combined first and second absorbent structures between the mating strip of the first drum and a plurality of bonding rolls or a belt.

17. The method of claim 16, wherein the absorbent material is a particulate superabsorbent polymer material.

18. The method of claim 16, wherein the step of applying adhesive is performed prior to the step of depositing absorbent material on the first supporting sheet.

19. The method of claim 16, wherein the step of applying adhesive is performed subsequent to the step of depositing absorbent material on the first supporting sheet.

20. The method of claim 16, wherein the mating strips of the first and second drums are made from silicone.

* * * * *